(12) United States Patent
Song et al.

(10) Patent No.: US 7,691,404 B2
(45) Date of Patent: Apr. 6, 2010

(54) TRANSDERMAL DELIVERY SYSTEM OF DICLOFENAC WITH IMPROVED WATER ABSORBABILITY AND ADHESION PROPERTIES

(75) Inventors: Jin Deog Song, Daejeon (KR); Dong-Won Kim, Daejeon (KR)

(73) Assignee: Samyang Corporation, Seoul (KR)

( * ) Notice: Subject to any disclaimer, the term of this patent is extended or adjusted under 35 U.S.C. 154(b) by 1303 days.

(21) Appl. No.: 10/415,628

(22) PCT Filed: Nov. 5, 2001

(86) PCT No.: PCT/KR01/01869

§ 371 (c)(1), (2), (4) Date: May 1, 2003

(87) PCT Pub. No.: WO02/36103

PCT Pub. Date: May 10, 2002

(65) Prior Publication Data

US 2004/0033254 A1 Feb. 19, 2004

(30) Foreign Application Priority Data

Nov. 6, 2000 (KR) .............................. 2000/65662

(51) Int. Cl.
*A61F 13/02* (2006.01)
*A61L 15/16* (2006.01)
*A61F 13/00* (2006.01)

(52) U.S. Cl. .................. 424/448; 424/449; 424/443

(58) Field of Classification Search .................. 424/448
See application file for complete search history.

(56) References Cited

U.S. PATENT DOCUMENTS

| 3,339,549 A | | 9/1967 | Morse | |
|---|---|---|---|---|
| 4,551,490 A | | 11/1985 | Doyle et al. | |
| 4,559,222 A | * | 12/1985 | Enscore et al. | 424/486 |
| 4,752,612 A | * | 6/1988 | Saito et al. | 514/420 |
| 4,844,902 A | * | 7/1989 | Grohe | 424/449 |
| 4,860,754 A | * | 8/1989 | Sharik et al. | 600/391 |
| 5,176,490 A | | 1/1993 | Ibe | |
| 5,494,680 A | * | 2/1996 | Peterson | 424/448 |
| 5,676,968 A | * | 10/1997 | Lipp et al. | 424/448 |
| 5,908,619 A | * | 6/1999 | Scholz | 424/78.02 |
| 6,495,160 B2 | * | 12/2002 | Esposito et al. | 424/451 |

(Continued)

FOREIGN PATENT DOCUMENTS

DE 19911262 A1 9/2000

(Continued)

OTHER PUBLICATIONS

Soluble Kollidon grades, Technical Information, Jan. 2004, Supersedes issue of Feb. 2001, pp. 1-14.*

(Continued)

*Primary Examiner*—Isis A Ghali
(74) *Attorney, Agent, or Firm*—Thorpe North & Western LLP

(57) ABSTRACT

An active agent containing adhesive composition suitable for transdermal drug delivery having excellent water absorbability which comprises an effective amount of an active agent, an acrylate adhesive, a polyvinylpyrrolidone having a molecular weight of 1,000,000-5,000,000; a polyvinylpyrrolidone having a molecular weight of 2,000-50,000; a non-ionic surfactant; a terpene; and a dissolution assistant.

15 Claims, 2 Drawing Sheets

U.S. PATENT DOCUMENTS

| | | | |
|---|---|---|---|
| 6,562,363 B1 * | 5/2003 | Mantelle et al. | 424/434 |
| 6,645,520 B2 * | 11/2003 | Hsu et al. | 424/449 |
| 6,723,337 B1 * | 4/2004 | Song et al. | 424/448 |

FOREIGN PATENT DOCUMENTS

| | | | |
|---|---|---|---|
| EP | 0201828 A2 | 5/1986 | |
| EP | 0343807 A2 | 5/1989 | |
| EP | 0591898 B1 | 10/1993 | |
| JP | 9104628 | 4/1997 | |
| JP | 10287530 A * | 10/1998 | |
| WO | WO 9916434 A1 * | 4/1999 | |
| WO | WO01/54674 A1 | 8/2001 | |

OTHER PUBLICATIONS

"Dermal and Transdermal Drug Delivery", Gurny et al., Nov. 1991.*

Satas, "Acrylic Adhesives" Handbook of Pressure-Sensitive Adhesive Technology, 2nded., pp. 396-456(D.Satas, ed.) Van Nostrand Reinhold, N.Y.(1989).

* cited by examiner

TRANSDERMAL DELIVERY SYSTEM OF DICLOFENAC WITH IMPROVED WATER ABSORBABILITY AND ADHESION PROPERTIES

This application is based on PCT/KR01/01869, which claims priority based on a Korean patent application No. 2000/65662, filed on Nov. 6, 2000.

FIELD OF THE INVENTION

The present invention relates to an adhesive based transdermal drug delivery system having improved water absorbability and adhesion properties. More particularly, the present invention relates to an adhesive based transdermal drug delivery system comprising a backing film, an adhesive matrix layer containing active ingredients, and a release liner which is peelable prior to use. The matrix layer of the present invention is a multilayered sandwich and comprises drug containing outer adhesive layers which adhere to the backing film and release liner respectively, between which is sandwiched an absorption enhancer layer. The adhesive layers comprise (a) an acrylate adhesive; (b) a mixture of high and low molecular weight polyvinylpyrrolidones, and (c) a colloidal silica. The absorption enhancer layer comprises non-ionic surfactants, terpenes and dissolution assistants. The transdermal drug delivery system of the present invention provides several desired improvements: excellent penetration of active ingredients through the skin; stable adhesion for extended periods of time to skin which is wet with perspiration; and no adhesive residue is left on the skin when the system is detached.

BACKGROUND OF THE INVENTION

Adhesives used for the transdermal drug delivery system include three categories: rubber adhesives (polyisobutylene rubber, styrene-isoprene copolymer etc.), silicon adhesives and acrylic adhesives.

Rubber adhesives have the advantage in that it is easy to control their physical properties by using various molecular weights of polymers and additives. However, rubber adhesives are highly hydrophobic and have poor adhesive properties in moisture rich environments, i.e. they adhere poorly to skin which is wet with perspiration.

In order to solve the above-mentioned problems, rubber adhesive compositions comprising a rubber polymer as a main component and a water-soluble hydrocolloid such as pectin, gelatin, and carboxymethylcellulose have been disclosed in U.S. Pat. Nos. 3,339,549, and 4,551,490 and European Patent 591 898. U.S. Pat. No. 5,176,490 also discloses a hydrocolloid adhesive composition comprising a base mainly composed of a hydrophobic polymer, water and a hydrophilic polymer. This adhesive, reportedly, has satisfactory water absorbability. However, the properties of the adhesive compositions mentioned above are merely suitable for plaster formulations that have a relatively large size, e.g. surface area, and thickness. When the adhesive layer absorbs water, the adhesive strength is significantly reduced and the plasters fail to remain attached. In addition, conventional plasters containing water-soluble polymers have poor adhesion when applied onto curved body parts for functional periods of time due to the thickness of the adhesive layer. Furthermore, conventional water-soluble plasters cannot be loaded with sufficient amounts of active ingredients because most drugs are poorly soluble in water. Therefore, plaster formulations are generally not suitable to be used as transdermal drug delivery devices.

Use of cross-linked polymers with hydrocolloids has been tried in order to maintain adhesive strength when the skin is wet. However, the results were not satisfactory in maintaining the adhesive strength. EP 0 343 807 A2 discloses a wound dressing comprising 30-65 wt. % of polyisoprene, 10-30 wt. % of a polyvinylpyrrolidone, 2-20 wt. % of a modified starch, 2-20 wt. % of pectin, 0.1-10 wt. % of an acrylic polymer, and 0-1 wt. % of fiber to control the absorption of water. In addition, EP 0 591 898 A1 discloses adhesive compositions for wound dressings comprising at least one hydrocolloid, hydrophobic unsaturated aliphatic polymers, and adhesive enhancers. However, the adhesive compositions mentioned above are comprised mainly of a rubber adhesive, as the adhesive component, which has high hydrophobicity. Therefore, they cannot be used for efficiently delivering active ingredients in their salt forms. In addition, they fail to maintain adhesive strength on skin that is wet.

Acrylic adhesives offer a number of advantages. For example, most drugs are more readily soluble in acrylic adhesives than in silicones and rubbers. Acrylic adhesives are highly compatible with or soluble in the commonly used skin penetration enhancers. In addition, the chemical properties of acrylic adhesives are easily manipulated to permit the preparation of both polar and non-polar adhesives. However, despite these advantages, acrylic adhesives are poorly soluble in water and have poor adhesion to skin which is wet with perspiration. Therefore, there is need for devices with improved adhesion properties, especially for delivering highly hydrophilic drugs.

SUMMARY OF THE INVENTION

The present invention provides an active agent containing adhesive composition with excellent water absorbability and suitability for the transdermal delivery of hydrophilic drugs. The transdermal drug delivery system containing the composition of the present invention provides for excellent penetration through the skin of the active ingredients and stable adhesion for extended periods of time to skin which is wet with perspiration. The transdermal drug delivery system comprises a backing film, a matrix layer containing active ingredients and a release liner that is peelable prior to use. The matrix layer of the transdermal drug delivery system is made up of outer adhesive layers comprising an active ingredient, a hydrophobic acrylic adhesive polymer, a mixture of high and low molecular weight water soluble polyvinylpyrrolidone (PVP) polymers and colloidal silica. Sandwiched between the adhesive layers is an absorption enhancing layer comprising ingredients selected from the group consisting of non-ionic surfactants, terpenes and dissolution assisting agents. Preferably, the matrix layer comprises 1-25 wt. % of an active ingredient; 10-95 wt. % of an acrylate adhesive; 1-7 wt. % of a polyvinylpyrrolidone having a molecular weight of 1,000,000-5,000,000 daltons; 1-13 wt. % of a polyvinylpyrrolidone having a molecular weight of 2,000-50,000 daltons; 0.1-25 wt. % of a non-ionic surfactant; 0.1-10 wt. % of a terpene; and 0.1-10 wt. % of a dissolution assistant.

One embodiment of the present invention relates to an active agent containing adhesive composition suitable for use in a matrix type transdermal patch comprising an effective amount of an active agent, an acrylate adhesive, a polyvinylpyrrolidone having a molecular weight of 1,000,000-5,000,000 daltons; a polyvinylpyrrolidone having a molecular weight of 2,000-50,000 daltons; a non-ionic surfactant; a terpene; and a dissolution assistant.

Another embodiment of the present invention relates to a matrix type transdermal drug delivery patch comprising:

(1) a backing layer,
(2) an active agent containing adhesive composition which is laminated into two adhesive layers, between which is sandwiched an absorption enhancer layer comprising volatile constituents as absorption enhancers; and
(3) a release liner which is peelable prior to use;

wherein said active agent containing adhesive composition comprises an effective amount of an active agent, an acrylate adhesive, a polyvinylpyrrolidone having a molecular weight of 1,000,000-5,000,000 daltons; a polyvinylpyrrolidone having a molecular weight of 2,000-50,000 daltons; a non-ionic surfactant; a terpene; and a dissolution assistant.

Another embodiment of the present invention relates to a transdermal drug delivery system comprising an active agent containing adhesive matrix composition, a backing material superimposed on one surface of the matrix composition, the backing material being substantially impermeable to the active agent and a peelable release liner superimposed on the surface of the matrix composition opposite the backing material, said matrix composition comprising an effective amount of an active agent, an acrylate adhesive, a polyvinylpyrrolidone having a molecular weight of 1,000,000-5,000,000 dalotns; a polyvinylpyrrolidone having a molecular weight of 2,000-50,000 daltons; a non-ionic surfactant; a terpene; and a dissolution assistant.

When applied to the skin, the present transdermal drug delivery system can absorb perspiration from the skin and maintain its adhesive strength. In addition, the present transdermal drug delivery system results in increased transdermal absorption of the active ingredient through the skin and causes reduced pain when it is removed from the skin. Additional features and advantages of the invention will be apparent from the detailed description, which follows, taken in conjunction with the accompanying drawings, which together illustrate, by way of example, features of the invention.

DETAILED DESCRIPTION OF THE INVENTION

Figure 1:
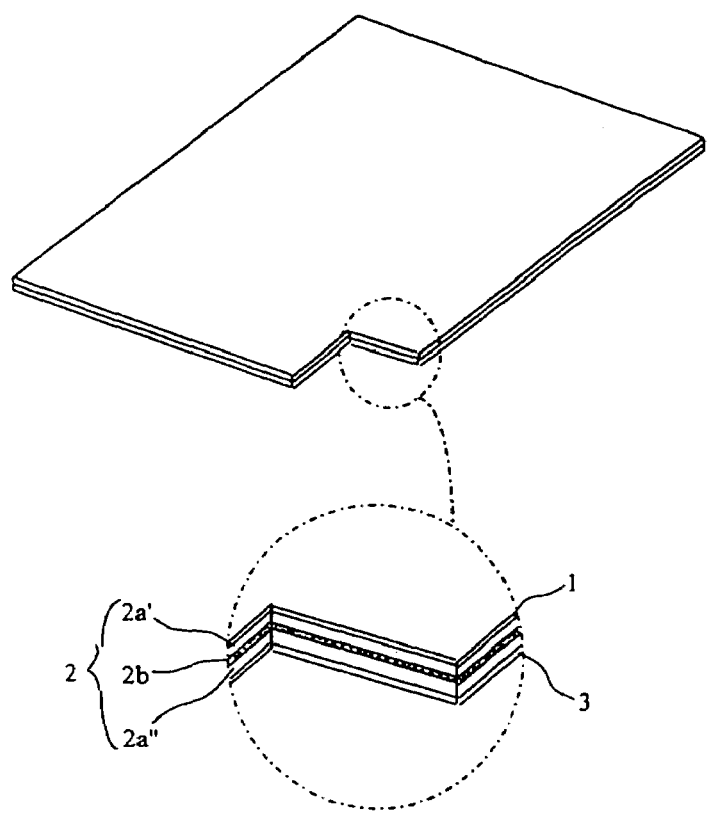
FIG. 1 is a cross-sectional view of the transdermal drug delivery system of the present invention.

Before the present composition and method for delivery of a bioactive agent are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a polymer containing "a layer" includes reference to two or more of such layers, reference to "a polymer" includes reference to one or more of such polymers, and reference to "a drug" includes reference to two or more of such drugs.

In describing and claiming the present invention, the following terminology will be used in accordance with the definitions set out below.

As used herein, the term "bioactive agent" or "drug" or any other similar term means any chemical or biological material or compound suitable for administration by methods previously known in the art and/or by the methods taught in the present invention and that induce desired biological or pharmacological effects, which may include but are not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating a disease from the organism. The effect may be local, such as providing for a local anaesthetic effect, or it may be systemic.

As used herein, "effective amount" means the amount of a nucleic acid or bioactive agent that is sufficient to provide the desired local or systemic effect and performance at a reasonable risk/benefit ratio as would attend any medical treatment.

As used herein, the term "pressure-sensitive adhesive" refers to a viscoelastic material which adheres instantaneously to most substrates with the application of very slight pressure and which remains permanently tacky. A polymer is a pressure-sensitive adhesive within the meaning of the term, as used herein, if it has the properties of a pressure-sensitive adhesive per se or functions as a pressure-sensitive adhesive by admixture with tackifiers, plasticizers or other additives.

The term "polyvinylpyrrolidone," or "PVP" refers to a polymer, either a homopolymer or copolymer, containing N-vinylpyrrolidone as the monomeric unit. Typical PVP polymers are homopolymeric PVPs and the copolymer vinyl acetate vinylpyrrolidone. The homopolymeric PVPs are known to the pharmaceutical industry under a variety of tradename designations including Povidone, Polyvidone, Polyvidonum, Polyvidonum soluble, and Poly(1-vinyl-2-pyrrolidone). The copolymer vinyl acetate vinylpyrrolidone is known to the pharmaceutical industry under various tradenames such as Copolyvidon, Copolyvidone, and Copolyvidonum.

The term "acrylic polymer" is used here, as in the art, interchangeably with "polyacrylate," "polyacrylic polymer," and "acrylic adhesive." The acrylate polymers useful in practicing the invention are polymers of one or more monomers of acrylic acids and other copolymerizable monomers. The acrylate polymers also include copolymers of alkyl acrylates and/or methacrylates and/or copolymerizable secondary monomers or monomers with functional groups. By varying the amount of each type of monomer added, the cohesive properties of the resulting acrylate polymer can be changed, as is known in the art. In general, the acrylate polymer is composed of at least 50% by weight of an acrylate or alkyl acrylate monomer, from 0 to 20% of a functional monomer copolymerizable with the acrylate, and from 0 to 40% of other monomers.

Acrylate monomers which can be used include acrylic acid, methacrylic acid, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate.

Functional monomers, copolymerizable with the above alkyl acrylates or methacrylates, which can be used include acrylic acid, methacrylic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate and methoxyethyl methacrylate. Further details and examples of acrylic adhesives which are suitable in the practice of the invention are described in Satas, "Acrylic Adhesives," Handbook of Pressure-Sensitive Adhesive Technology, 2nd ed., pp. 396-456 (D. Satas, ed.), Van Nostrand Reinhold, N.Y. (1989). Suitable acrylic adhesives are commercially available and include the polyacrylate adhesives sold under the trademarks Duro-Tak 80-1194, Duro-Tak 80-1196, and Duro-Tak 80-1197 by National Starch and Chemical Corporation, Bridgewater, N.J. Other suitable acrylic adhesives are those sold under the trademarks Gelva-Multipolymer Solution (GMS) 737 or 788 (Monsanto; St. Louis, Mo.).

Agents known to accelerate the delivery of the drug through the skin have been referred to as skin-penetration enhancers, accelerants, adjuvants, and absorption promoters, and are collectively referred to herein as "enhancers." This class of agents includes those with diverse mechanisms of action including those which have the function of improving the solubility and diffusibility of the drug within the multiple polymers and those which improve percutaneous absorption, for example, by changing the ability of the stratum corneum to retain moisture, softening the skin, improving the skin's permeability, acting as penetration assistants or hair-follicle openers or changing the state of the skin including the boundary layer. Some of these agents have more than one mechanism of action, but in essence they serve to enhance the transdermal delivery of the drug.

Some examples of enhancers are polyhydric alcohols such as dipropylene glycol, propylene glycol, and polyethylene glycol which enhance drug solubility; oils such as olive oil, squalene, and lanolin; fatty ethers such as acetyl ether and oleyl ether; fatty acid esters such as isopropyl myristate which enhance drug diffusibility; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide, and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin; and the drugs to be administered. Other agents include oleic and linoleic acids, ascorbic acid, panthenol, butylated hydroxytoluene, tocopherol, tocopheryl acetate, tocopheryl linoleate, propyl oleate, and isopropyl palmitate.

"Colloidal silica" refers to fine micro particles of silicon dioxide dispersed in water. The size of the particles in colloidal silica is generally in the range of about 1 to 100 nm.

Reference will now be made to the exemplary embodiments and specific language will be used herein to describe the same. It will nevertheless be understood that no limitation of the scope of the invention is thereby intended. Alterations and further modifications of the inventive features illustrated herein, and additional applications of the principles of the invention as illustrated herein, which would occur to one skilled in the relevant art and having possession of this disclosure, are to be considered within the scope of the invention.

The present invention is described in more detail as set forth hereunder.

The present invention provides a pressure-sensitive adhesive composition suitable as a matrix for use in a transdermal drug delivery system. As noted above, this matrix layer is made up of two outer adhesive layers comprising an effective amount of an active ingredient, an acrylate adhesive polymer, a polyvinylpyrrolidone having a molecular weight of 1,000,000-5,000,000 daltons and a polyvinylpyrrolidone having a molecular weight of 2,000-50,000 daltons. Associated between the outer layers dose a middle penetration enhancer layer comprising a non-ionic surfactant, a terpene, and a dissolution assistant.

In reference to FIG. 1, one embodiment of the present invention relates to a transdermal drug delivery system which comprises a backing layer (1), an adhesive matrix layer (2) having active ingredients, and a release liner (3) which is peelable prior to use. The matrix layer (2) comprises 1-25 wt. % of an active ingredient, 40-95 wt. % of an acrylate adhesive, 1-7 wt. % of a polyvinylpyrrolidone having a molecular weight of 1,000,000-5,000,000 daltons, 1-13 wt. % of a polyvinylpyrrolidone having a molecular weight of 2,000-50,000 daltons, 0.1-25 wt. % of a non-ionic surfactant, 0.1-10 wt. % of terpene, and 0.1-10 wt. % of a dissolution assistant.

Each component of the transdermal drug delivery system of the present invention is described in more detail as set forth hereunder.

The matrix layer having the active ingredient of the present invention comprises an acrylate adhesive as a major component, a mixture of high and low molecular weight polyvinylpyrrolidones and colloidal silica. The matrix layer having the active ingredient of the present invention can absorb perspiration from the skin, retain its adhesiveness for extended periods of time after absorbing water such as perspiration, and be detached from the skin without pain and without leaving residues behind.

Preferably, the adhesive polymer of the present invention is a copolymer of acrylate and vinylacrylate or an acrylate polymer having carboxyl (—COOH) and hydroxyl (—OH) functional groups, which has superior adhesiveness as compared to a rubbery polymer or water-soluble acrylic polymer. In addition, the adhesive polymers used in the present invention have high solubility in organic solvents which increases the concentration of the active ingredient contained within the matrix. Therefore, the matrix layer is thin with a high concentration of the active ingredients contained therein which helps increase transdermal absorption efficiency and results in superior adhesion for long-term application onto the skin. Furthermore, due to the thin adhesive layer containing the active ingredient, the drying process of the adhesive layer can be achieved in a short period of time, which in turn significantly reduces the manufacturing time and cost. As for the adhesion constituent, pressure sensitive adhesives such as acrylic polymers are selected. The amount of acrylic polymers contained in the matrix layer is preferably within the range of 40-95 wt % of the total weight of the matrix layer. If the amount of the adhesion constituent is more than 95 wt %, the matrix cannot contain sufficient amounts of active ingredients, absorption enhancers and dissolution assistants. If the amount of the adhesion constituent is less than 40 wt %, the matrix layer can not provide for appropriate epidermal adhesion.

The present invention is particularly useful for transdermal delivery of diclofenac diethylammonium salt. The active ingredient amount contained in the matrix is preferably within the range of 1-25 wt % based on the total weight of the matrix layer. If the amount of the active ingredient is less than 1 wt %, the transdermal absorption of the drug is significantly reduced due to the low drug concentration. On the other hand, if the amount is more than 25 wt %, the active ingredient within the patch is likely to precipitate from the matrix layer.

In the present invention, water-soluble polymers such as polyvinylpyrrolidones are contained in the adhesive layer in order to maintain adhesiveness after absorbing water. The optimum adhesiveness can be obtained by controlling the strength of the acrylate adhesive layer and amount and rate of perspiration absorbed from the skin. Therefore, the adhesive layer of the transdermal drug delivery system of the present invention can maintain its adhesion, even after exposure to perspiration, after a long period of time and it leaves no residues on the skin.

Polyvinylpyrrolidones have been used for a long time for hair lotions such as shampoo and mousse, cosmetics and bath goods, since they reduce skin irritation. It has been also disclosed that use of a mixture of polyvinylpyrrolidones and polyethylene polymers relieves skin irritation. Since polyvinylpyrrolidones are highly soluble in water, they can absorb a good amount of water per unit weight compared to other water-soluble polymers such as hydrocolloids.

The present invention uses a mixture of high and low molecular weight polyvinylpyrrolidones in the adhesive layer of the transdermal drug delivery system in order to maintain adhesion to wet skin. The adhesive layer of the present invention maintains its adhesive properties to skin even after absorbing moisture. Low molecular weight polyvinylpyrrolidones absorb moisture faster than high molecular weight polyvinylpyrrolidones. However, high molecular weight polyvinylpyrrolidones can reinforce the adhesive strength by entangling homogeneously between the long side chains of the polyvinylpyrrolidone and acrylate adhesive polymers. These entangled polyvinylpyrrolidones are advantageous in maintaining adhesive strength, even after absorbing moisture.

In the present invention, the amount of the polyvinylpyrrolidone varies depending on the physical properties desired of the adhesive layer. However, it is preferred that the amount of polyvinylpyrrolidone is within the range of from 5 to 20 wt. % of the total weight of the matrix, this amount provides excellent adhesive strength and initial tackiness. If the amount of the polyvinylpyrrolidone is less than 5 wt. %, it is not sufficient to provide the desired effect. On the other hand, if it is more than 20 wt. %, the initial tackiness of the adhesive layer may be significantly reduced.

The effects of the polyvinylpyrrolidone on the adhesive properties are controlled by the molecular weight of the polyvinylpyrrolidones used and it is preferred to use a mixture of polyvinylpyrrolidones having a low molecular weight, 2,000-50,000 daltons, and polyvinylpyrrolidones having a high molecular weight, 1,000,000-5,000,000 daltons.

Examples of polyvinylpyrrolidone having high molecular weight include commercialized Povidones 90F of BASF Corporation which has a molecular weight within the range of 1,000,000-5,000,000 daltons. High molecular weight polyvinylpyrrolidones reinforce the adhesive strength and reduce the movement of active ingredients when used with an acrylate adhesive. It is preferable that the transdermal drug delivery matrix of the present invention contain 1-10 wt %, more preferably 1-7 wt % of the total weight of the matrix, of the high molecular weight polyvinylpyrrolidone. If it is used in less than 1 wt %, it is not sufficient to provide the desired effect. If it is used in more than 10 wt %, the adhesiveness may be significantly reduced.

Examples of polyvinylpyrrolidones having low molecular weights include commercialized Povidones 12PF and Povidones 25K. When used with an acrylate adhesive, Povidones 12PF and Povidones 25K show little effect on reinforcing the adhesive strength between adhesive layers, but their adhesiveness is reduced less compared with use of Povidone 90F. Preferably, 5-15 wt %, and more preferably 6-13 wt % of low molecular weight polyvinylpyrrolidones to the total matrix composition are used. If used with more than the desired amount, such as 15 wt %, it absorbs too much moisture and thus reduces the adhesive strength and results in pain when detached from the skin. However, if used in less than the desired amount, such as 5 wt %, it is not sufficient to provide the desired effect.

The present invention also employs colloidal silica in order to reduce pain when the adhesive is detached from the skin. Since the adhesiveness of the transdermal drug delivery system of the present invention is greatly enhanced by the usage of polyvinylpyrrolidones in an acrylate adhesive, pain may result when the patch is detached from the skin. Therefore a colloidal silica is used to reduce, to some degree, the adhesiveness which will help reduce pain when it is detached from the skin but increase adhesive strength between the adhesive and the absorption enhancer layers. In the present invention it is appropriate to include the colloidal silica in an amount of 0.5-5 wt % to the total composition, more preferably 1.5-4 wt %. If the amount is less than 0.5 wt %, it is hard to obtain the desired effect. On the other hand, if the amount is more than 5 wt %, the initial tackiness is significantly reduced and the efficiency of manufacturing the composition becomes inferior.

The preceding paragraphs describe the adhesive polymer portion of the matrix which is generally divided into two layers, e.g. a first layer which will be laminated to a backing film of the transdermal system and a second layer which will be laminated to a peelable release liner.

In addition, the transdermal drug delivery system also contains an enhancer layer sandwiched between the polymer layers and comprises a non-ionic surfactant, a terpene, and a dissolution assistant as absorption enhancers. The absorption enhancers increase the absorption of the active ingredient into the skin, in a manner directly proportional to the amount present, up to a certain concentration. However, use of the absorption enhancers above such a concentration tends to irritate the skin instead of enhance absorption.

The terpene suitable for the present invention is preferably a member selected from the group consisting of menthol, D-limonene, geraniol, nerolidol, and a mixture thereof. The amount of terpene used for the present invention is preferably within the range of 0.1-10 wt % of the total weight of the matrix layer. Examples of non-ionic surfactants include glyceryl mono-oleate, glyceryl mono-laurate, sorbitan mono-oleate, glyceryl tri-oleate, isopropyl myristate, and a mixture thereof. The non-ionic surfactant is preferably used in an amount of 0.1-25 wt % of the total weight of the matrix layer. Furthermore, a dissolution assistant is added therein to increase the solubility of the active ingredient in the matrix layer. Suitable dissolution assistants can be selected from the group consisting of triacetin, isopropyl alcohol, propylene glycol, dimethylacetamide, propylene carbonate, diethylethanolaine, diethyl amine, triethylamine, N-methyl morphorine, benzammonium chloride, and a mixture thereof, which is added in an amount of 0.1-10 wt % to the total weight of the matrix layer.

One embodiment of the present invention provides a combination of a non-ionic surfactant, a terpene and a dissolution assistant which shows excellent transdermal penetration.

Examples include combinations of menthol/glyceryl monolaurate/propylene glycol; menthol/glycerin mono-laurate/propylene glycol; menthol/sorbitan mono-oleate/triacetin and isopropyl alcohol; menthol/sorbitan monooleate/propylene glycol; and menthol/glyceryl mono-laurate/triacetin.

Another embodiment of the present invention is a drug containing adhesive matrix patch which comprises: 1-20 wt. % of an active ingredient, 65-90 wt. % of an acrylate adhesive, 0.1-5 wt. % of menthol, 10-20 wt. % of sorbitan mono-oleate, 2-20 wt. % of a polyvinylpyrrolidone, 0.5-5 wt. % of colloid silica, and 0.1-5 wt. % of triacetin or propylene glycol as a dissolution assistant. The transdermal drug delivery system as such is shown to have superior transdermal penetration and adhesion.

In a device aspect of the invention, the pressure-sensitive adhesive composition can be used as the adhesive portion of any transdermal drug delivery system (e.g., a reservoir device) or it can comprise a drug containing adhesive matrix patch. Of course, the principles of the invention would still apply to embodiments where the dermal composition is not a pressure-sensitive adhesive and comprises a drug reservoir.

The transdermal drug delivery system of the present invention comprises a backing film (1), a matrix layer (2) containing active ingredients, and a release liner (3) which is peelable prior to use.

Reference to FIG. 1 shows a schematic illustration of the drug containing adhesive matrix patch embodiment of the invention. The transdermal drug delivery system comprises a drug containing adhesive matrix (2) of a defined geometric shape with a protective release liner (3), which is peelable prior to use, on one side of the drug containing adhesive matrix (2) and a backing film (1) on the other side. Removal of the release liner (3) exposes the pressure-sensitive multiple polymer adhesive matrix which functions both as the drug carrier matrix and as the means of applying the system to the patient. The matrix layer (2) comprises adhesive layers which contain active ingredients and non-volatile constituents and are laminated into two layers (2a', 2a"). Between the two adhesive layers (2a', 2a"), an absorption enhancer layer (2b) which comprises enhancing constituents such as non-ionic surfactants, terpenes and dissolution assistants are inserted therein.

A device, or individual dosage unit, of the present invention can be produced in any manner known to those of skill in the art. After the dermal composition is formed, it may be brought into contact with the backing layer in any manner known to those of skill in the art. Such techniques include calender coating, hot melt coating, solution coating, etc. Of course, backing materials are well known in the art and can comprise plastic films of polyethylene, vinyl acetate resins, ethylene/vinyl acetate copolymers, polyvinyl chloride, polyurethane, and the like, metal foils, non-woven fabric, cloth and commercially available laminates. The backing material generally has a thickness in the range of 2 to 1000 micrometers and the dermal composition is generally disposed on backing material in a thickness ranging from about 12 to 250 micrometers. Preferably, the backing film (1) of the present invention is a non-woven fabric or film comprising polymer substrates chosen from polyurethane, polyester, polyethylene and rayon which are suitable for curved body parts. In addition, the adhesive layer adjacent to the backing film may be manufactured by using adhesive only.

Furthermore, the present invention uses an acrylate adhesive instead of a water-soluble polymer in order to dissolve active ingredients at high concentrations, and consequently a relatively thin adhesive layer of less than 30 µm is incorporated into the matrix layer (2). As for the release liner (3), a disposable drug-impermeable film that is commonly used in the manufacture of patches is utilized. Suitable release liners are also well known in the art and include the commercially available products of Dow Corning Corporation designated Bio-Release.RTM. liner and Syl-off.RTM. 7610 liner.

The configuration of the transdermal delivery system of the present invention can be any shape or size as is necessary or desirable. Illustratively, a single dosage unit may have a surface area in the range of 1 to 200 cm$^2$.

In a method aspect of the invention, the adhesive polymers are blended (but not chemically reacted or cross-linked) with high molecular weight PVP, low molecular weight PVP, as well as with the drug and other ingredients to result in a drug containing pressure-sensitive adhesive composition. The term "blending," of course, incorporates choosing the appropriate polymeric components, and the proportions thereof, to achieve the desired effect. In a preferred embodiment of the invention, a transdermal drug delivery system is prepared by mixing a mixture of high and low molecular weight PVPs, a polyacrylate adhesive, a drug, co-solvent(s), and a tackifying agent, if needed, in an appropriate volatile solvent(s), then casting the mixture and removing the solvent(s) by evaporation thereby forming a film. Suitable volatile solvents include, but are not limited to, alcohols such as isopropanol and ethanol; aromatics such as xylenes and toluene; aliphatics such as hexane, cyclohexane, and heptane; and alkanoic acid esters such as ethyl acetate and butyl acetate.

The order of the steps, the amount of the ingredients, and the amount and time of agitation or mixing may be of importance as process variables which will depend on the specific polymers, drugs, co-solvents, and enhancers used in the formulation. These factors can be adjusted by those skilled in the art, while keeping in mind the objective of providing a uniform product. It is believed that a number of other methods, including changing the order of some of the steps, can be carried out and still give desirable results. In addition to having various shapes, the dosage units produced may come in various sizes. A surface area in the range of 1 to 200 square centimeters is contemplated, and the presently preferred sizes are: 5, 10, 15, 20, 30, 30 and 60 square centimeters.

The present invention herein is explained in more detail by the following examples. The following examples will enable those skilled in the art to more clearly understand how to practice the present invention. It is to be understood that, while the invention has been described in conjunction with the preferred specific embodiments thereof, that which follows is intended to illustrate and not limit the scope of the invention. Other aspects of the invention will be apparent to those skilled in the art to which the invention pertains.

EXAMPLES 1-17 AND COMPARATIVE EXAMPLE 1

A transdermal drug delivery system was manufactured according to the following method, and the compositions of the matrix layer (2) are shown in Tables 1-3.

Into a 50 ml sample bottle, diclofenac diethylammonium salt, polyvinylpyrrolidone (Povidone 90F, Povidone 25K), and colloidal silica (Aerosil 380, 200, Degussa Co.) were placed. After addition of a non-ionic surfactant and ethanol, the mixture was stirred at 40° C. until the pharmaceutical compositions were completely dissolved. The mixture solution was cooled to room temperature and an acrylate adhesive agent (National Starch & Chemical Co., Durotak™, 87-2852, 87-2196, 87-4098) was placed therein. The solution was stirred to mix all the constituents in the sample bottle and tehn allowed to stand for 20 min to remove air bubbles. Thereafter, a lab coater and dryer (Mathis Co. of Switzerland) were used to laminate the mixture onto both a backing film (1) and a release liner film (3) to form adhesive layers (2a') and (2a") and then dried at a temperature range of 80-120° C. for 10 min.

The backing film (1), as in FIG. 1, and the adhesive layer (2a') containing the pharmaceutical compositions were formed by laminating the aforementioned mixture onto a backing film (1) (3M® non-woven polyurethane 9905, 3M® non-woven polyester 1538, 3M® rayon non-woven 1533, 3M® rayon acetate 1588, MSP® 501 of Dongsung Chemical Co.).

On top of the release liner film (3) (3M Scotchpak® 1022, 3M® paper release liner 1361, 9743), adhesive layer (2a") was formed by the same method as used for the aforementioned adhesive layer (2a'). The volatile absorption enhancer layer (2b) was formed by directly dispersing or coating, via a nozzle onto the dried adhesive layer (2a"), an appropriate amount of a solution which was prepared by mixing a solution of a terpene and a dissolution assistant. By means of a dispersing via coating method, the impregnation of appropriate amounts of a terpene and a dissolution assistant into the adhesive constituent was possible.

A transdermal drug delivery system was manufactured by laminating layers (2a') and (2a") together such that enhancer layer (2b) was sandwiched between them. A moisture vapor absorption test of the respective transdermal drug delivery system manufactured as aforementioned was carried out at 38° C. at a relative humidity of 90%; the moisture vapor transmission rate (MVTR) was measured according to the ASTM D-1653 method; the tackiness was measured according to the ASTM D-2979 method (Polyken™ probe tack tester); the adhesive strength was determined by measuring the time until the adhesive layer, measuring 12.5×25.4 mm and applied to stainless steel, failed when a mass of 1 Kg was suspended therefrom; the easiness of detachment from skin was determined by measuring the strength required to release the adhesive layer, measuring 12.5×25.4 mm and applied to stainless steel, at a rate of 250 mm/min; and the efficiency was determined by measuring the pain produced by detachment from the skin and the amount of adhesive residue left behind. The results are summarized in Tables 1-3.

TABLE 1

| | Category | Com. Ex. 1 | Example 1 | 2 | 3 | 4 | 5 |
|---|---|---|---|---|---|---|---|
| Composition constituent of matrix layer (wt. %) | Diclofenac diethylammonium | 18.5 | 18.5 | 18.5 | 18.5 | 18.5 | 18.5 |
| | Sorbitan mono-oleate | 20.0 | 20.0 | 20.0 | 20.0 | 20.0 | 20.0 |
| | Polyvinylpyrrolidone (Povidone 90F) | — | 1.5 | 3.0 | 5.0 | 5.0 | 8.0 |
| | Polyvinylpyrrolidone (Povidone 25K) | — | 1.5 | 3.0 | 5.0 | 8.0 | 8.0 |
| | Colloidal silica (Aerosil 380) | — | — | — | — | — | — |
| | Triacetin | 0.7 | 0.7 | 0.7 | 0.7 | 0.7 | 0.7 |
| | 1-Menthol | 1.5 | 1.5 | 1.5 | 1.5 | 1.5 | 1.5 |
| | Durotak ™ 87-2852 | 51.9 | 49.3 | 46.6 | 43.1 | 40.5 | 37.9 |
| | Durotak ™ 87-4098 | 7.4 | 7.0 | 6.7 | 6.2 | 5.8 | 5.4 |
| properties | Moisture absorbability (after 24 hrs, %) | 2.1 | 5.5 | 9.7 | 12.3 | 16.7 | 20.3 |
| | Moisture absorbability (after 24 hrs, %) | 2.1 | 5.5 | 9.7 | 12.3 | 16.7 | 20.3 |
| | Initial tackiness (g/cm$^2$) | 338 | 286 | 223 | 182 | 130 | 65 |
| | Tackiness after absorbing moisture (g/cm$^2$) | 155 | 260 | 245 | 204 | 208 | 258 |
| | Holding time (min) | 72 | 150 | 450 | 1176 | 1290 | — |
| | Peel adhesion at 180° of removal (g/in) | 650 | 680 | 720 | 797 | 852 | 917 |
| | Moisture vapor transmission rate (g/m$^2$/day) | 250 | 400 | 525 | 670 | 850 | 1020 |
| | Adhesive residue[1] (after 24 hrs adhered, n = 10) | 2.0 | 2.5 | 2.7 | 3.2 | 3.5 | 3.6 |
| | Pain[2] when released (after 24 hrs adhered, n = 10) | 2.8 | 2.7 | 2.4 | 2.4 | 2.0 | 1.5 |

[1] value of adhesive residues: a lot = 1, some = 2, a little = 3, no residue = 4
[2] pain when it is released: very severe = 1, severe = 2, mild = 3, no pain = 4

As shown in Table 1, the moisture absorbability, moisture vapor transmission rate and adhesive strength (holding time) were proportional to the amount of polyvinylpyrrolidone present from 0 to 16 wt. % as shown in Examples 1-5 and Comparative Example 1.

Figure 2:
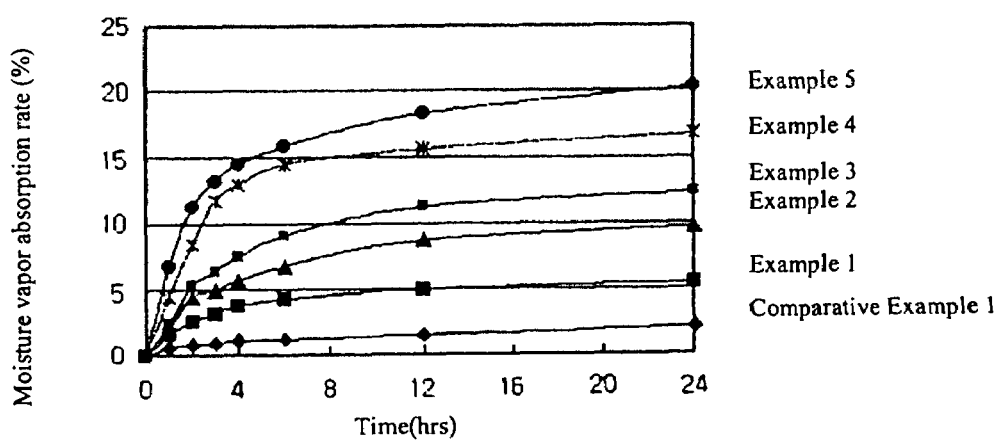
FIG. 2 is a graph showing the moisture vapor absorption rate of the transdermal drug delivery system containing polyvinylpyrrolidones over time.
Figure 3:
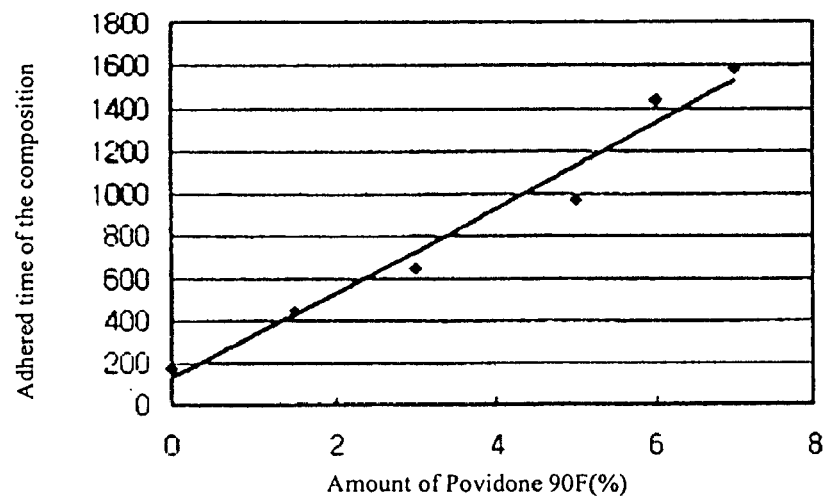
FIG. 3 is a graph showing the holding time of the transdermal drug delivery system containing polyvinylpyrrolidone (Povidone 90F) (Examples 6-11).

As shown in Table 1 and FIG. 2, it is noted that the polyvinylpyrrolidone provided for excellent adhesion to skin that was wet by absorbing moisture within a short period of time. But when the amount of polyvinylpyrrolidone used was more than 25 wt. %, the initial tackiness was significantly reduced. The peel strength at 180° of removal and the pain caused by detachment from the skin were severe. This is due to the increased adhesion by the polyvinylpyrrolidones after they absorb moisture. Examples containing more than the expected amount of polyvinylpyrrolidones showed high alterations in adhesive strength between the initial tackiness and that after absorbing moisture.

TABLE 2

| Category | | Example 6 | 7 | 8 | 9 | 10 | 11 |
|---|---|---|---|---|---|---|---|
| Composition constitution of matrix layer (wt. %) | diclofenac diethylammonium | 18.5 | 18.5 | 18.5 | 18.5 | 18.5 | 18.5 |
| | Sorbitan mono-oleate | 20.0 | 20.0 | 20.0 | 20.0 | 20.0 | 20.0 |
| | Polyvinylpyrrolidone (Povidone 90F) | 0.0 | 1.5 | 3.0 | 5.0 | 6.0 | 7.0 |
| | Polyvinylpyrrolidone (Povidone 25K) | 13.0 | 11.5 | 10.0 | 8.0 | 7.0 | 6.0 |
| | Colloidal silica (Aerosil 380) | — | — | — | — | — | — |
| | Triacetin | 0.7 | 0.7 | 0.7 | 0.7 | 0.7 | 0.7 |
| | l-Menthol | 1.5 | 1.5 | 1.5 | 1.5 | 1.5 | 1.5 |
| | Durotak ™ 87-2852 | 40.5 | 40.5 | 40.5 | 40.5 | 40.5 | 40.5 |
| | Durotak ™ 87-4098 | 5.8 | 5.8 | 5.8 | 5.8 | 5.8 | 5.8 |
| properties | Moisture absorbability (after 24 hrs, %) | 16.8 | 16.2 | 16.5 | 17.2 | 16.5 | 17.3 |
| | Initial tackiness (g/cm$^2$) | 155 | 147 | 140 | 133 | 101 | 74 |
| | Moisture absorbability (after 24 hrs, %) | 16.8 | 16.2 | 16.5 | 17.2 | 16.5 | 17.3 |
| | Initial tackiness (g/cm$^2$) | 155 | 147 | 140 | 133 | 101 | 74 |
| | Tackiness after absorbing moisture (g/cm$^2$) | 245 | 237 | 229 | 233 | 240 | 228 |
| | Holding time (min) | 180 | 450 | 650 | 970 | 1,430 | — |
| | Peel adhesion at 180° of removal (g/in) | 932 | 815 | 798 | 814 | 809 | 775 |
| | Moisture vapor transmission rate (g/m$^2$/day) | 898 | 872 | 843 | 852 | 790 | 750 |
| | Adhesive residue[1] (after 24 hrs adhered, n = 10) | 2.3 | 2.7 | 3.2 | 3.5 | 3.6 | 3.7 |
| | Pain[2] when released (after 24 hrs adherence, n = 10) | 2.1 | 2.4 | 2.5 | 2.3 | 2.1 | 2.4 |

[1]value of adhesive residues: a lot = 1, some = 2, a little = 3, no residue = 4
[2]pain when released: very severe = 1, severe = 2, mild = 3, no pain = 4

Table 2 represents the properties which are dependent upon the ratios of high molecular weight polyvinylpyrrolidone and low molecular weight polyvinylpyrrolidone used. Examples 6-11 contain 13 wt. % of polyvinylpyrrolidones, the holding time and adhesive residue left behind were significantly reduced with increase in the amount of Povidone 90F having a molecular weight of 1,000,000 used. The adhesive strength was found to be proportional to the amount of Povidone 90F used. The moisture absorbability and moisture vapor transmission rate were similar but the peel adhesion at 180° for removal and pain caused were increased due to an increase in the adhesive strength of the polyvinylpyrrolidones after absorbing moisture.

TABLE 3

| Category | | Example 12 | 13 | 14 | 15 | 16 | 17 |
|---|---|---|---|---|---|---|---|
| Composition constituent of matrix layer (wt. %) | diclofenac diethylammonium | 18.5 | 18.5 | 18.5 | 18.5 | 18.5 | 18.5 |
| | Sorbitan mono-oleate | 20.0 | 20.0 | 20.0 | 20.0 | 20.0 | 20.0 |
| | Polyvinylpyrrolidone Povidone 90F) | 5.0 | 5.0 | 5.0 | 5.0 | 5.0 | 5.0 |
| | Polyvinylpyrrolidone (Povidone 25K) | 8.0 | 8.0 | 8.0 | 8.0 | 8.0 | 8.0 |
| | Colloidal silica (Aerosil 380) | 1.0 | 1.0 | 1.0 | 1.0 | 1.0 | 1.0 |
| | Triacetin | 0.7 | 0.7 | 0.7 | 0.7 | 0.7 | 0.7 |
| | l-Menthol | 1.5 | 1.5 | 1.5 | 1.5 | 1.5 | 1.5 |
| | Durotak ™ 87-2852 | 39.6 | 38.8 | 37.9 | 37.0 | 36.1 | 35.3 |
| | Durotak ™ 87-4098 | 5.7 | 5.5 | 5.4 | 5.3 | 5.2 | 5.0 |
| Properties | Moisture absorbability (after 24 hrs, %) | 16.4 | 16.9 | 17.1 | 17.3 | 17.2 | 18.1 |
| | Initial tackiness (g/cm$^2$) | 135 | 130 | 127 | 110 | 95 | 87 |
| | Tackiness after absorbing moisture (g/cm$^2$) | 205 | 130 | 148 | 135 | 115 | 108 |
| | Holding time (min) | 1,250 | 1,340 | 1,405 | 1,350 | 1,270 | 1,583 |

TABLE 3-continued

| | Example | | | | | |
|---|---|---|---|---|---|---|
| Category | 12 | 13 | 14 | 15 | 16 | 17 |
| Peel adhesion at 180° of removal (g/in) | 540 | 340 | 245 | 255 | 267 | 250 |
| Moisture vapor transmission rate(g/m$^2$/day) | 851 | 870 | 885 | 897 | 900 | 917 |
| Adhesive residue[1] (after 24 hrs adhered, n = 10) | 3.7 | 3.9 | 3.9 | 3.8 | 3.9 | 3.9 |
| Pain[2] when it is released (after 24 hrs adhered, n = 10) | 3.2 | 3.7 | 3.9 | 3.8 | 3.9 | 3.9 |

[3]value of adhesive residues: a lot = 1, some = 2, a little = 3, no residue = 4
[4]pain when released: very severe = 1, severe = 2, mild = 3, no pain = 4

Figure 4:
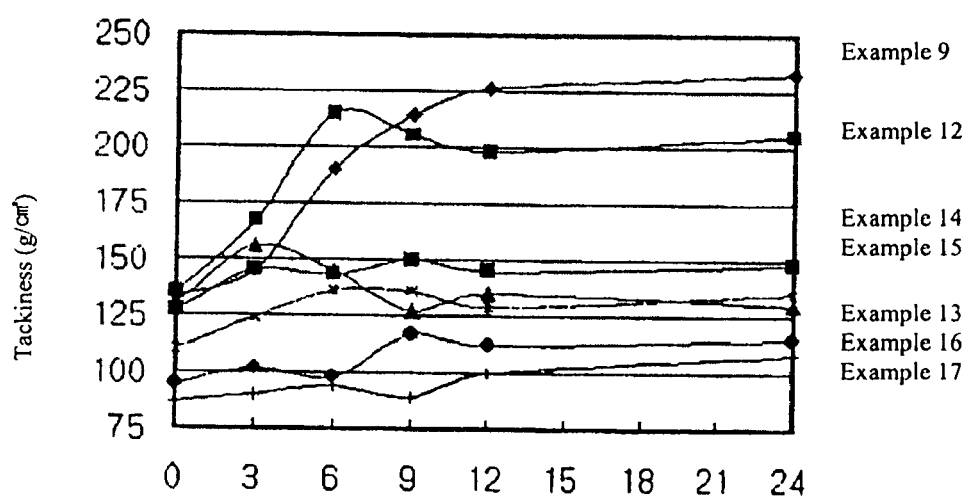
FIG. 4 is a graph showing the tackiness after absorbing moisture by the transdermal drug delivery system containing colloidal silica (Examples 9, and 12-17).

The properties were compared after addition of colloidal silica to the compositions of Table 2 and Table 3. As shown in FIG. 4, the adhesive strength rapidly increases with absorption of moisture by the composition of Example 10. When colloidal silica is contained in the transdermal drug delivery composition, rapid increases in adhesive strength resulting from absorption of moisture was prevented and less pain was produced by detachment from the skin. When the colloidal silica used was more than 5 wt. %, the adhesive strength was significantly reduced and problems were encountered in the manufacturing process. Therefore, it is preferred not to use more than 5 wt. %.

As shown above, by mixing water-soluble polyvinylpyrrolidone compounds having optimized ratios of high molecular weight and low molecular weight PVPs in an acrylic adhesive, the transdermal drug delivery system, according to the present invention, can absorb perspiration well and maintain adhesive strength to skin after absorbing moisture. Furthermore, the addition of colloidal silica enables the transdermal drug delivery system of the present invention to reduce the pain caused by detachment from the skin. In addition, absorption enhancers and dissolution assistants at a certain mixing ratio, as disclosed in the aforementioned method, provide enhanced transdermal penetration of the active ingredient. Therefore, the transdermal drug delivery systems according to the present invention have several advantages. For example, they increase transdermal penetration of the active ingredients, enhance wear and adhesion onto curved body parts, absorb perspiration well while maintaining the adhesive strength, and reduce the pain caused by detachment from the skin without leaving adhesive residues on the skin.

We claim:

1. An active agent containing adhesive composition suitable for use in a matrix type transdermal patch consisting essentially of 1-25 wt. % of an active agent selected from the group consisting of diclofenac diethylammonium and diclofenac diethylanimonium salt, 40-95 wt. % of an acrylate adhesive, 1-7 wt. % of a polyvinylpyrrolidone having a molecular weight of 1,000,000-5,000,000; 1-13 wt. % of a polyvinylpyrrolidone having a molecular weight of 2,000-50,000; 0.1-25 wt. % of a non-ionic surfactant; 0.1-10 wt. % of a terpene; 0.1-10 wt. % of a dissolution assistant; and 0.5-5 wt. % of colloidal silica.

2. The composition according to claim 1, wherein said acrylate adhesive is an acrylate polymer or a copolymer of acrylate and vinyl acetate.

3. The composition according to claim 1, wherein said non-ionic surfactant is selected from the group consisting of glyceryl mono-oleate, glyceryl mono-laurate, sorbitan mono-oleate, glyceryl tri-oleate, isopropyl myristate, and a mixture thereof.

4. The composition according to claim 1, wherein said terpene is selected from the group consisting of menthol, D-limonene, geraniol, nerolidol, and a mixture thereof.

5. The composition according to claim 1, wherein said dissolution assistant is triacetin, isopropyl alcohol, propylene glycol, dimethylacetamide, propylene carbonate, diethylethanolaine, diethyl amine, triethylamine, N-methyl morphorine, benzylammonium chloride, and a mixture thereof.

6. A transdermal drug delivery system comprising an active agent containing adhesive matrix composition, a backing material superimposed on one surface of the matrix composition, the backing material being substantially impermeable to the active agent and a peelable release liner superimposed on the surface of the composition opposite the backing material, said matrix composition consisting essentially of 1-25 wt. % of an active agent selected from the group consisting of diclofenac diethylammonium and diclofenac diethylammonium salt, 40-95 wt. % of an acrylate adhesive, 1-7 wt. % of a polyvinylpyrrolidone having a molecular weight of 1,000,000-5,000,000; 1-13 wt. % of a polyvinylpyrrolidone having a molecular weight of 2,000-50,000; 0.1-25 wt. % of a non-ionic surfactant; 0.1-10 wt. % of a terpene; and 0.1-10 wt. % of a dissolution assistant; and 0.5-5 wt. % of colloidal silica.

7. The transdermal drug delivery system according to claim 6, wherein said acrylate adhesive is an acrylate polymer or a copolymer of an acrylate polymer and vinyl acetate.

8. The transdermal drug delivery system according to claim 6, wherein said non-ionic surfactant is selected from the group consisting of glyceryl mono-oleate, glyceryl mono-laurate, sorbitan mono-oleate, glyceryl tri-oleate, isopropyl myristate, and a mixture thereof.

9. The transdermal drug delivery system according to claim 6, wherein said terpene is selected from the group consisting of menthol, D-limonene, geraniol, nerolidol, and a mixture thereof 10. The transdermal drug delivery system according to claim 6, wherein said dissolution assistant is triacetin, isopropyl alcohol, propylene glycol, dimethylacetamide, propylene carbonate, diethylethanolaine, diethyl amine, triethylamine, N-methyl morphorine, benzylammonium chloride, and a mixture thereof.

11. A matrix type transdermal drug delivery patch comprising:
(1) a backing layer,
(2) an active agent containing adhesive composition which is laminated into two adhesive layers, between which is sandwiched an absorption enhancer layer comprising volatile constituents as absorption enhancers; and (3) a release liner which is peelable prior to use;

wherein said active agent containing adhesive composition consists essentially of 1-25 wt. % of an active agent selected from the group consisting of diclofenac diethylammonium and diclofenac diethylammonium salt, 40-95 wt. % of an acrylate adhesive, 1-7 wt. % of a polyvinylpyrrolidone having a molecular weight of 1,000,000-5,000,000; 1-13 wt. % of a polyvinylpyrrolidone having a molecular weight of 2,000-50,000; 0.1-25 wt. % of a non-ionic surfactant; 0.1-10 wt. % of a terpene; 0.1-10 wt. % of a dissolution assistant; and 0.5-5 wt. % of colloidal silica.

12. The matrix type transdermal drug delivery patch of claim 11, wherein said acrylate adhesive is an acrylate polymer or a copolymer of an acrylate polymer and vinyl acetate.

13. The matrix type transdermal drug delivery patch of claim 11, wherein said non-ionic surfactant is selected from the group consisting of glyceryl mono-oleate, glyceryl monolaurate, sorbitan mono-oleate, glyceryl tri-oleate, isopropyl myristate, and a mixture thereof.

14. The matrix type transdermal drug delivery patch of claim 11, wherein said terpene is selected from the group consisting of menthol, D-limonene, geraniol, nerolidol, and a mixture thereof.

15. The matrix type transdermal drug delivery patch of claim 11, wherein said dissolution assistant is triacetin, isopropyl alcohol, propylene glycol, dimethylacetamide, propylene carbonate, diethylethanolaine, diethyl amine, triethylamine, N-methyl morphorine, benzylammonium chloride, and a mixture thereof.

* * * * *